Figure 1A:
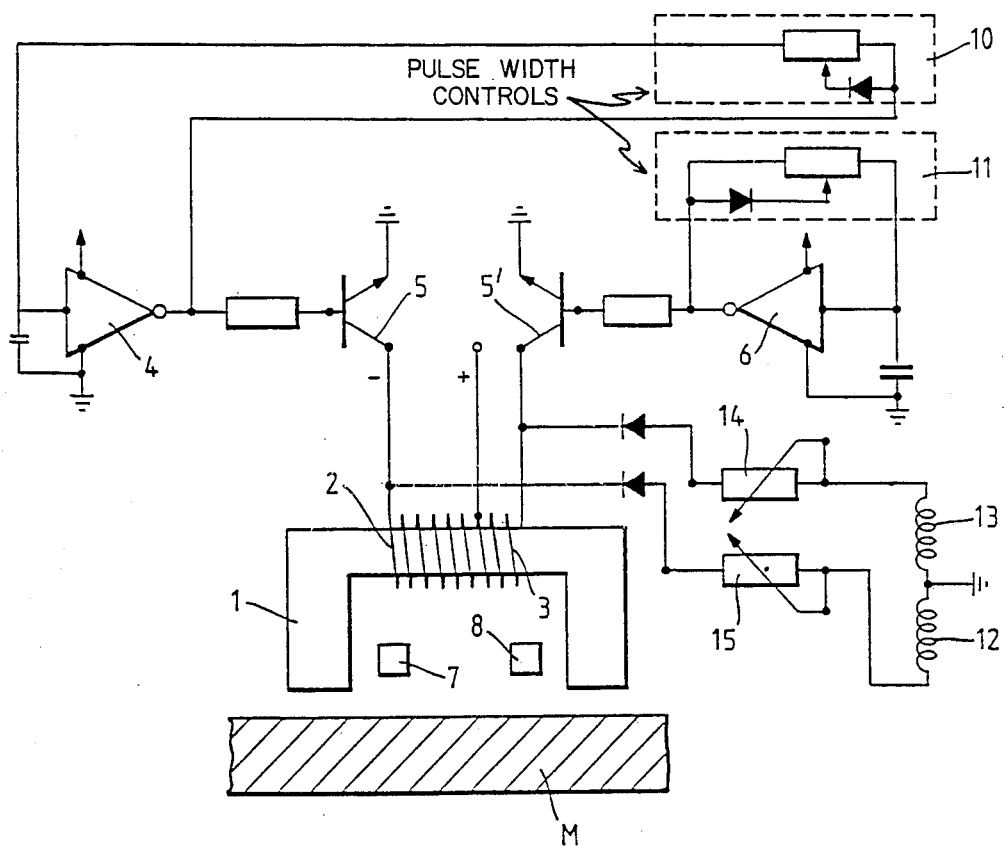

United States Patent [19]

Olsen et al.

[11] Patent Number: 4,931,730

[45] Date of Patent: Jun. 5, 1990

[54] METHOD AND APPARATUS FOR NON-DESTRUCTIVE MATERIALS TESTING AND MAGNETOSTRUCTURAL MATERIALS INVESTIGATIONS

[75] Inventors: Terje Olsen, Loddefjord; Nils C. Lekven, Os; Julius Hartai, Drammen, all of Norway

[73] Assignee: Dam Patent A/S, Kokstad, Norway

[21] Appl. No.: 112,837

[22] PCT Filed: Feb. 16, 1987

[86] PCT No.: PCT/NO87/00014

§ 371 Date: Oct. 15, 1987

§ 102(e) Date: Oct. 15, 1987

[87] PCT Pub. No.: WO87/05112

PCT Pub. Date: Aug. 27, 1987

[30] Foreign Application Priority Data

Feb. 17, 1986 [NO] Norway ................................ 860591

[51] Int. Cl.⁵ .................... G01B 7/24; G01N 27/80; G01N 27/82; G01R 33/12
[52] U.S. Cl. .................... 324/209; 324/227; 324/232; 324/239; 324/240; 324/243; 73/779; 73/862.69
[58] Field of Search ............... 324/209, 217, 218, 222, 324/223, 226, 227, 228, 229, 232, 233, 234–243, 260; 73/779, 862.36, 862.69

[56] References Cited

U.S. PATENT DOCUMENTS

| | | | |
|---|---|---|---|
| 2,098,064 | 11/1937 | Pfaffenberger | 324/240 |
| 3,742,357 | 6/1973 | Kubo et al. | 324/209 |
| 3,825,819 | 7/1974 | Hansen et al. | 73/150 A |
| 4,495,465 | 1/1985 | Tomaiuolo et al. | 324/232 |
| 4,497,209 | 2/1985 | Kwun et al. | 324/209 X |

FOREIGN PATENT DOCUMENTS

| | | | |
|---|---|---|---|
| 0096078 | 12/1983 | European Pat. Off. | 324/209 |
| 2746477 | 4/1978 | Fed. Rep. of Germany | 324/209 |
| 2837733 | 3/1980 | Fed. Rep. of Germany | 324/209 |
| 3516214 | 11/1983 | Fed. Rep. of Germany | 324/209 |
| 0728071 | 4/1980 | U.S.S.R. | 324/209 |
| 1249274 | 10/1971 | United Kingdom | 324/209 |
| 1266248 | 3/1972 | United Kingdom | 324/209 |
| 1267434 | 3/1972 | United Kingdom | 324/209 |
| 2012966 | 8/1979 | United Kingdom | 324/209 |

*Primary Examiner*—Gerard R. Strecker
*Assistant Examiner*—Warren S. Edmonds
*Attorney, Agent, or Firm*—Merchant, Gould, Smith, Edell, Welter & Schmidt

[57] ABSTRACT

A method and apparatus for generating and detecting magnetization responses from ferromagnetic, ferrimagnetic, paramagnetic, or diamagnetic materials comprises a means for generating an alternating magnetic field. The cycle of the alternating magnetic field includes a first magnetization pulse and a second demagnetization pulse, the energy content of the magnetization pulse and the demagnetization pulse being approximately equal, the time duration of the magnetization pulse being substantially longer than the time period of the magnetization pulse, the demagnetization pulse having a higher magnetic field strength than the magnetization pulse magnetic field strength. The effect of the alternating magnetic field on the material to be tested is measured by magnetic field detectors. The field detectors generate electrical signals which are fed to an oscilloscope, a comparator, or a computer for analysis. Characteristics of the material to be tested which are measured by the device include rotation of the magnetic domains, alignment of magnetic domains, alignment of magnetic moments, the Barkhausen effect, coercive force, remanence, material structure, stress fields, and defects.

11 Claims, 4 Drawing Sheets

METHOD AND APPARATUS FOR NON-DESTRUCTIVE MATERIALS TESTING AND MAGNETOSTRUCTURAL MATERIALS INVESTIGATIONS

The present invention concerns a method and apparatus for non-destructive materials testing and more particularly a method and apparatus for magnetostructural materials investigations of diamagnetic, paramagnetic, ferromagnetic and ferrimagnetic materials.

Several methods for non-destructive testing of materials are at present known in the art, like radiography by means of X-rays, gamma rays or particle radiation, ultrasonic testing, acoustic emission testing, eddycurrent testing etc. These methods are applied in a number of circumstances, typically for instance in non-destructive testing of structural materials. The results obtained by such methods are usually based on indirect measuring methods, and although these may be quite straightforward, their interpretation is based on empirical procedures and related to materials' properties and defects by means of a calibration against specimens and thus liable to errors when the test specimens have properties and defects not accounted for by empirically obtained calibration data. Moreover, signal/noise ratios are often too poor to allow for a more precise structural analysis, for instance of crystalline properties of the materials, lattice defects, dislocations, stress fields and the like.

In prior art there are known methods based on measuring the magnetic properties of the materials to be tested, and devices have been developed and used to this end. Most of these methods are based on magnetizing the materials and recording either the magnetization curve commonly known as the B-H-graph, or the hysteresis loop. This allows the determination of parameters as magnetic remanence or the coercive force, which may be related to mechanical properties of the materials by empirical calibration. Remanence and coercive force may for instance be related to the hardness of a material, as they to some extent are dependent on grain structure, which determines the hardness of the specific material. They may also be correlated with the tensile strength of the material to a fairly accurate degree. Small discontinuities or jumps may show up in the magnetization curve and the size and number of these jumps, which are known as the Barkhausen effect, may be measured and analyzed to show the existence of defects, cracks and voids in the material. As well known to those skilled in the art, the Barkhausen effect is due to the movement of the so-called domain (Bloch) walls in a ferromagnetic material, a movement which is strongly affected by lattice defects, dislocations, precipitations, inclusions, cracks and voids, thus giving an indication of stress fields and grain properties. These phenomena all contribute to observe the discontinuities of the magnetization curve. Recording and analyzing the Barkhausen effect may thus furnish important information about the properties of materials. Another method of magnetic testing relies on applying a magnetic flux to a material and recording the remanent flux pattern of the material. Defects in the material may then show up as a distortion of the flux pattern. The use of magnetic measurement, for instance measuring the change of the magnetic field strength, has been applied to thickness testing of material, e.g. in metallurgical industry, where control of the thickness of rolled or extruded products is wanted.

Magnetic methods as mentioned above are for instance stated and disclosed in DE-OS No. 27 36 477, which discloses the detection of defects in magnetic materials, based on an analysis of noise signals generated by the Barkhausen effect, EP 96 078 disclosing on-line hardness testing of steel sheet by means of measuring remanence, GC Patent No. 1 266 248, which discloses determination of the carbon content of iron alloys by means of a hardness measurement based on recording the coercive force and U.S. Pat. No. 4,495,465, which discloses the use of magnetic flux in non-destructive testing by detecting a variation of the flux pattern indicating a variation in reluctance and thus the occurrence of defects.

Magnetic testing methods as disclosed in the above-mentioned patents are usually limited to the testing of materials that are easily magnetizable, i.e., ferromagnetic or ferrimagnetic materials. However, nearly all materials and elements do react to an external, applied magnetic field, whether they are magnetizable or not.

The purpose of the present invention is to provide a new, non-destructive testing method for all materials or elements that can be magnetized, however weakly, i.e., all substances where the constituent atomic particle possess a magnetic moment. To be more specific, the present invention provides a method of testing substances or materials which either may be diamagnetic, paramagnetic, ferromagnetic or ferrimagnetic. For a general rule survey of the nature of magnetism and the magnetic properties of these substances one may refer to general text books and reference works like R. Feynman, The Feynman Lectures on Physics, Vol. II (1964), ch. 34, Sections 1–6, ch. 36, CH. 37; William T. Scott, The Physics of Electricity and Magnetism (1959), ch. 8; McGrawHill Encyclopedia of Science and Technology: articles on "Ferromagnetism", "Magnetic materials" (latest edition).

In particular, it is the purpose of the present invention to provide a method for analyzing in depth the structure and properties of the aforementioned materials. Still more particularly it is the purpose of the present invention to provide a fast and reliable testing method by recording the response of material to an external magnetic field and basing the evaluation of the measurements on a quantitative analysis of the recorded response curve, avoiding sources of error generated by noise and measurement uncertainties.

The above-mentioned purpose is achieved by means of a method and apparatus characterized by the features of the appended claims.

The method of the present invention is called a magneto-structural method, as it provides information of the structure of the tested materials by recording the counterinduction generated by rotation of magnetic domains or alignment of magnetic moments in the test specimen in response to an external, alternating magnetic field applied to the specimen. The magnetostructural method according to the invention is thus characterized by magnetizing and demagnetizing a test specimen of the material, preferably of a small volume, for instance by means of an electromagnet as defined by an apparatus for performing the method of the invention, which apparatus will be described in detail later. As the applied magnetic filed is an alternating field, magnetization and demagnetization take place within the period of the field. The magnetization pulse has a substantially longer duration than the demagnetization pulse, for instance from 1 ms to 100 ms, as against 10 ns to 10 ms.

The energy content of the magnetization pulse is kept equal to the energy content of the demagnetization pulse, such that the power of each pulse of each half-cycle of the filed period will be unequal, the demagnetization pulse having the greater power. As the magnetic field strength is proportional to the power, it is readily seen that the demagnetization will take place with a greater field strength than the magnetization. During demagnetization the response in the form of counterinduction from the test specimen is detected by suitable detectors and recorded by suitable recording instruments. It is essential that the initial magnetic state of the specimen, i.e., the magnetic state at the beginning of the magnetization, is reestablished at the end of the demagnetization process. In a test cycle the frequency of the magnetizing/demagnetizing cycle is kept constant, while the half-cycles of the period are regulated such that they are asymmetric with respect to time and magnetic field strength. A longer magnetization pulse ensures that sufficient saturation is obtained, while a short (and hence) powerful demagnetization pulse evokes the strongest counterinduction response possible with a high signal/noise ratio. This is particularly advantageous when testing materials that are weakly magnetizable. Test cycles with different frequencies may be obtained by varying the frequency of the alternating field. The field strength of the alternating field may also be varied, likewise the asymmetry of the half-cycles with respect to time and power. Further, each half-cycle may be given an asymmetric energy content, i.e., the energy of the magnetizating pulse is set different from that of the demagnetizing pulse. In this way it is possible to evoke different responses from the test specimen. The time and frequency parameters of the recorded response curves may then be analyzed to furnish important information about the properties of the material; information which is not obtainable when using magnetization/demagnetization cycles with unvarying frequency and power. Increasing the frequency may for instance show the time response of the rotation of the domains of the aligning of magnetic moments, which may be useful in a structural analysis. (One should note that the prediction of material structures and properties from magnetic measurable quantities and vice versa are notoriously difficult, the main reason for this being that magnetic effect are completely quantum mechanical phenomena and cannot be computed with any degree of accuracy, nor understood in terms of classical physics). In this connection see R. M. White, Quantum Theory of Magnetism, 2d ed., Spring 1983.

For diamagnetic materials the magnetostructural structural method of the invention will yield information about structure (phases), lattice defects, dislocations, cracks, pores and stress fields. These materials have a very low permeability which is linear, and requires sensitive detectors in order to measure the counterinduction response. The magnetization and demagnetization yield an infinitesimal hysteresis loop with a differential permeability. The same circumstances apply to paramagnetic materials, and the same information is obtained. It should, however, be noted that the magnetization of paramagnetic materials is temperature dependent.

The ferromagnetic and ferrimagnetic materials are preferably magnetized in a region where the magnetic permeability is high. This is advantageous if one also decides to record the Barkhausen effect in addition to the counterinduction in order to obtain further information about materials structure and defects, as the Barkhausen effect is much more pronounced in the so-called soft magnetic region of the magnetization curve. In order to reach this region an un-magnetized ferromagnetic or ferrimagnetic test specimen may be subjected to a steady DC magnetic field, upon which the alternating field may be superimposed. One should, however, note that applying the alternating field alone will generate a residual magnetic field in the test specimen, thus increasing its magnetization until countered by the growing reluctance of the specimen. However, it is not prerequisite that the testing takes place in the high permeability region as the use of sensitive detectors allow the measurements to be made, e.g., in the initial hard magnetic region. The hysteresis loop will then be essentially infinitesimal, otherwise one may obtain a minor loop with an incremental permeability. Coercive force and remanence may be measured in the usual way.

The detection of internal defects as cracks, voids, precipitations and inclusions are easily achieved during the demagnetization, where such defects show up in the demagnetization curves as discontinuities. In such testing it will be advantageous to calibrate empirically the curve against results obtained with a standard specimen with known properties. In order to detect stress fields the test specimens are kept at rest. By comparing the evolution of stress fields one may be able to detect fatigue in the test material, even when the test specimen is a permanently located structural member, as the testing may be performed in situ with suitable apparatus. Further, the method of the invention may be used with specimens that are moved relatively to the apparatus, for instance by translation or rotation, whereby it will be possible to locate defects and detect spatial variations in the materials structure. Thus, for ferromagnetic and ferrimagnetic materials a variety of parameters may be measured by the magnetostructural method of the invention in addition to the detection and recording of counter induction.

Figure 1B:
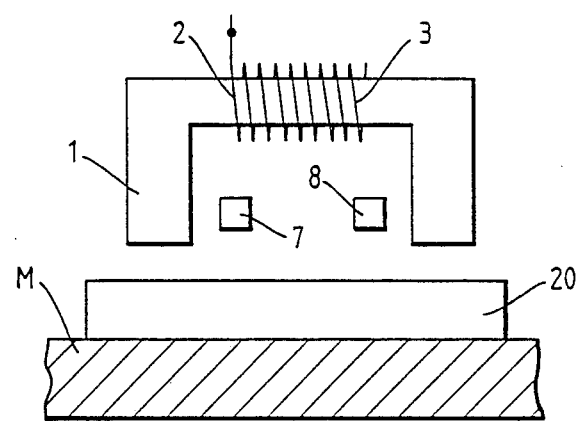
Figure 2:
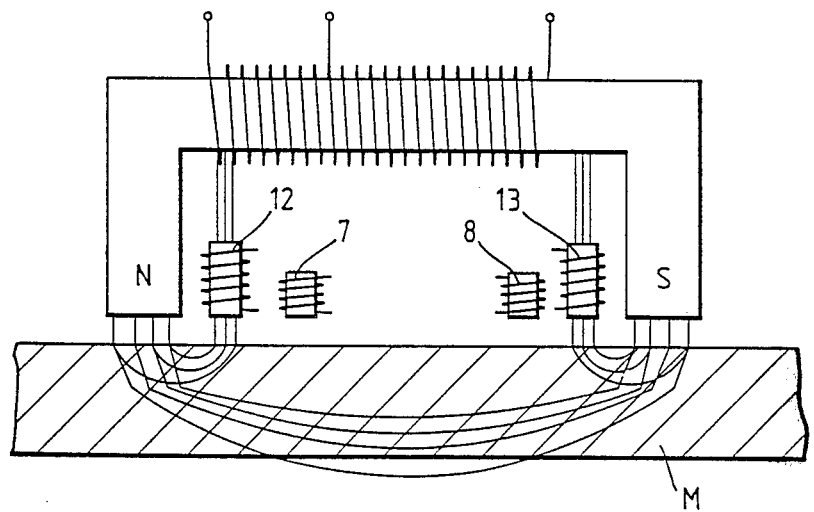
Figure 3:
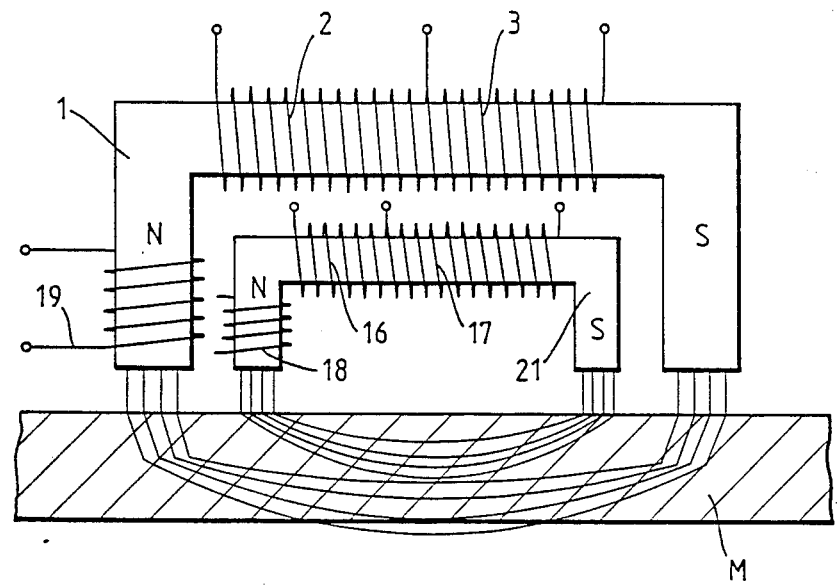

The apparatus according to the invention will now be described in greater detail by means of preferred embodiments shown in the drawing, where FIG. 1a is a schematic view showing the block diagram of an apparatus of the present invention, FIG. 1b is an alternative embodiment of the test arrangement according to the invention, FIG. 2 is detailed view showing an embodiment of the magnetizing device of the apparatus, and FIG. 3 is a modified embodiment of the magnetizing device.

Magnetizing and demagnetizing of a test specimen M is achieved by means of a per se known electromagnet 1, which for instance may have a U-shape as shown in FIG. 1a or be formed as a rod or ring. FIG. 1 thus shows a U-shaped ferrite core for magnetization, with a coil 2 and a coil 3. The apparatus comprises an oscillator consisting of a driver circuit 4 for pulse width control and a transistor 5 driven by the drive circuit 4 and connected to the coil 2, which for instance may have three times as many turns as the coil 3, which in turn is connected to driver circuit 6 via a second transistor 5'. The oscillators may either possess a common voltage or they may have a controlled voltage supply in order to control the field strength. The pulse width controls 10 and 11 provides a predetermined duration of the magnetization pulse and the demagnetization pulse, respectively.

Above the test specimen M and inside the magnet 1 there are arranged two detectors 7 and 8, as shown in FIG. 1a. The detectors should have a very high magnetic sensitivity, but they may also be composed of small ferrite cores with coils in order to detect the dynamic strength change in the test specimen M, or they may be high sensitivity detecting coils for detecting counterinduction. The signals from the detectors may be fed to an oscilloscope, a comparator or a computer for either a simple comparison of the detector pulses in order to ascertain discrepancies between the pulses in case the apparatus is used for the detection of defects in the material, or in the case of more complicated structural analyses, the output of the detectors is treated to a more sophisticated analysis by means of mathematical methods.

In order to achieve measurements with the apparatus arranged at some distance from the test specimen or in order to achieve a matter depth penetration of the specimen, auxiliary coils 12, 13 are provided to distribute the magnetic field from the electromagnet, i.e., the magnetic pulse emitter, to a desired distance or depth in the material by using the variable resistors 14, 15 (FIG. 2). The emitter/detector system is independent of distance variation because the output signal essentially shows an amplitude variation only, whereas the frequency variation is very small, such that a analysis of the detector output may be performed regardless of the amplitude. In this way a substantial improvement of the signal/noise ratio is achieved in comparison with other magnetic or inductive methods. By changing the relation between the magnetizing and demagnetizing current in the emitting coils by means of the individually controllable oscillator voltage, other properties of the test specimen may be investigated, such as remanence and permeability in martensitic or austenitic materials. Residual stresses after welding and heat treatment as well as structural defects of the material may be detected in the same way.

The incremental permeability and the magnetic flux of the material to be investigated may be changed by placing a piece of magnetic material 20 as shown in FIGS. 1b and 1c.

A measurement of thickness of a material, for instance a wall thickness, may advantageously be done by using a magnetizing device as shown in FIG. 3. The measurement of wall thickness is thus performed, as shown, with two large U-shaped ferrite cores arranged within each other. The ferrite core 1 is thereby provided with three coils 2, 3, 19. The second ferrite core 21 is likewise provided with three coils 16, 17 and 18. The cores 1 and 21 are spaced at a certain distance relatively to the specimen to be investigated. The coils 2 and 3 are each connected to an oscillator as shown in FIG. 1. The oscillators now control the parameters of the pulses emitted by the coils 2, 3, such that the material is completed demagnetized. The ferrite core 5 is formed in the same way as the ferrite core 1, but is given smaller physical dimensions in order to be located within the ferrite core 1. The coils 2, 3, and 16, 17 work in phase, but with different field strength, depending on materials type and wall thickness, and with the same polarity.

The coils 18 and 19 are the detector coils, and their output is similarly fed to a comparator or a computer for analysis. With a suitable field strength relation in the emitter coils the detector coils will detect the same amplitude and the same wave form. Variation of the wall thickness will cause the magnetic field from the core 1 to leave the material and magnetic losses are reduced, thus causing the amplitude detected in the detector coil 14 to increase in proportion to the reduction of the wall thickness.

We claim:

1. A method for magnetostructural materials investigation and non-destructive materials testing of diamagnetic, paramagnetic, ferromagnetic and ferrimagnetic materials, comprising the steps of:
   (a) generating an alternating magnetic field, the period of which is comprised of a first half-cycle being a magnetization pulse and a second half-cycle being a demagnetization pulse;
   (b) regulating the pulse period of the alternating magnetic field such that the duration of the magnetization pulse is substantially larger than the duration of the demagnetization pulse, whereby the demagnetization pulse has a greater magnetic field strength than the magnetization pulse;
   (c) placing the material to the investigated in the alternating magnetic field such that the material in the case of ferromagnetic or ferrimagnetic materials is magnetized and demagnetized and in the case of diamagnetic or paramagnetic materials is magnetically excited;
   (d) measuring the counterinduction generated by the induction or the magnetic response of the material to be investigated; and
   (e) recording the time dependence of the measured counterinduction.

2. A method according to claim 1 further comprising the step of regulating the alternating magnetic field by varying the frequency of the alternating magnetic field.

3. A method according to claim 1, further comprising the steps of measuring the Barkhausen effect, the coercivity force or the remanence in ferromagnetic or ferrimagnetic materials; and recording the time dependency of such measured value.

4. A method according to claim 1 further comprising the step of regulating the strength of the alternating magnetic field such that the energy content of the magnetization pulse is substantially different from the energy content of the demagnetization pulse.

5. A method according to claim 1 further comprising the step of regulating the strength of the alternating magnetic field such that energy content of the magnetization pulse is approximately equal to the energy content of the demagnetization pulse.

6. A method according to claim 1, wherein the material to be investigated is ferromagnetic or ferrimagnetic, characterized in magnetizing and demagnetizing the material in the soft magnetic region of the hysteresis loop of the material or in a region of the hysteresis loop where the magnetic permeability of the material is high, the alternating field in such period generating a minor hysteresis loop with incremental permeability.

7. A method according to claim 6, characterized in inserting a piece of ferromagnetic material, which may be a permanent magnet, between the material to be investigated and the origin of the alternating magnetic field, thus changing the incremental permeability and the magnetic flux of said material.

8. A method according to claim 1, characterized in performing the investigation of the material simultaneously with moving the material relatively to the magnetic field, preferably by translation or rotation.

9. An apparatus for performing the method according to claim 1, characterized in comprising at least one electromagnet provided with ferrite core and preferably 2 coils, located adjacent to a specimen of the material to be investigated; the coils of the electromagnet being connected to a pulse width controlled oscillator; each coil being provided preferably with one oscillator for controlling the duration of the magnetization pulses and the demagnetization pulses; and detectors for performing the measurements, the detector outputs being connected to a recording device, such as an oscilloscope, a comparator or a computer.

10. An apparatus according to claim 8, characterized in that auxiliary coils are provided adjacent to the end regions of the ferrite cores facing the specimen to achieve a deeper penetration or to allow the testing to take place at greater distance between the cores and the specimens the field strength of the auxiliary coils being regulated to interact with the magnetic field of the electromagnet.

11. An apparatus according to claim 10, characterized in that two uniform ferrite cores are provided, one inside the other, the coils of the two ferrite cores working in phase, but with different field strengths, for performing thickness measurements.

* * * * *